United States Patent [19]
Summaria et al.

[11] Patent Number: 6,139,878
[45] Date of Patent: Oct. 31, 2000

[54] METHOD FOR PREPARING A DIAFILTERED STABILIZED BLOOD PRODUCT

[75] Inventors: Louis Summaria, Villa Park; Nathan Roth, Bourbonnais; Aberash Berhe, Bourbonnais; Mark Even, Bourbonnais, all of Ill.

[73] Assignee: Aventis Behring, LLC, King of Prussia, Pa.

[21] Appl. No.: 09/066,694

[22] Filed: Apr. 27, 1998

[51] Int. Cl.⁷ .................................................. A61K 35/14
[52] U.S. Cl. ........................ 424/529; 424/532; 424/533; 435/2
[58] Field of Search .................. 424/529, 532, 424/533; 435/2

[56] References Cited

U.S. PATENT DOCUMENTS

| | | | |
|---|---|---|---|
| 4,420,398 | 12/1983 | Castino | 210/641 |
| 4,702,829 | 10/1987 | Polaschegg et al. | 210/195.2 |
| 4,728,430 | 3/1988 | DiLeo et al. | 210/639 |
| 4,863,609 | 9/1989 | Schnabel et al. | 210/641 |
| 4,917,799 | 4/1990 | Masuda et al. | 210/435 |
| 4,978,453 | 12/1990 | Leonard | 210/636 |
| 5,213,814 | 5/1993 | Goodrich, Jr. et al. | 424/532 |
| 5,651,966 | 7/1997 | Read et al. | 424/93.72 |

OTHER PUBLICATIONS

Bixler et al. Chem. Eng. Progr., Symp. Ser. 64(84): 90–103 (1968). Abstract, 1968.

Weinstein R. et al., "Survival of Lyophilized and Reconstitued Human Red Blood Cells In Vivo"; Transfus Clin. Biol. 1995; 2(6); pp. 427–432.

Takahashi R. et al., "Degradation of Macromolecules During Preservation of Lyophilized Pathological Tissues"; Pathol. Res. Pract. Jun. 1995; 191(5); pp. 420–426.

Chao, FC. et al., "Infusible Platelet Membrane Microvesicles: A Potential Transfusion Substitute for Platelets"; Transfusion. Jun. 1996; 36(6); pp. 536–542.

*Primary Examiner*—Jean C. Witz
*Attorney, Agent, or Firm*—Ostrolenk, Faber, Gerb & Soffen, LLP

[57] ABSTRACT

A method using diafiltration to prepare a blood product is described. The method removes contaminating plasma proteins from whole blood or blood products. Diafiltration may be used on paraformaldehyde-fixed platelets to remove formaldehyde to undetectable levels, and to suspend the platelets into a formulation buffer suitable for subsequent treatment, such as lyophilization. The manufacturing procedure can be divided into three steps, a first diafiltration, fixation, preferably with paraformaldehyde, and a second diafiltration. In the first step, plasma proteins are removed from fresh or stored platelets or blood cells. The technique is gentle to prevent the activation and aggregation of the platelets. Fixation stabilizes the platelets to withstand freezing, lyophilization and subsequent reconstitution, and also provides a viral and bacterial reduction. The second diafiltration removes the paraformaldehyde to undetectable levels, and suspends the platelets or blood cells into a formulation buffer for subsequent lyophilization.

20 Claims, 4 Drawing Sheets

METHOD FOR PREPARING A DIAFILTERED STABILIZED BLOOD PRODUCT

BACKGROUND OF THE INVENTION

1. Field of the Invention

The present invention relates to blood products and methods of preparation. More specifically, the present invention relates to the preparation of stabilized blood products using diafiltration.

2. Description of the Related Art

Platelets are anucleate cells that circulate in the blood in a resting form. They are the cellular component of the blood coagulation mechanism. Upon stimulation at a site of vascular injury, platelets adhere to the injured surface and undergo a complex series of biochemical and morphological alterations, resulting in secretion of stored granular components and formation of platelet aggregates. Platelet adhesion and aggregation, through interaction with fibrin, results in the formation of a primary platelet plug. Plasma coagulation is further accelerated by the increased availability of platelet membrane phospholipid surfaces that concentrate clotting factors and activate coagulant proteins at the injured hemorrhagic site.

Platelets currently are used in clinical settings to treat various conditions, including hemorrhagic shock and thrombocytopenia. Thrombocytopenia is characterized by an abnormally small number of platelets in the circulating blood. The condition can be induced in patients by heparin use, infections, auto-antibodies, malaria, lymphoma, hepatitis, radiation exposure, and chemotherapeutic agents.

Administration of a platelet preparation can also be utilized to treat certain genetic disorders that result in impaired platelet function. In addition, diafiltered stabilized blood product preparations can be used in the surgical repair of trauma involving extensive blood loss, such as for treatment of gun shot and knife combat victims.

Current therapeutic blood product transfusion therapy is hampered in the clinical setting by the short (five day) shelf life of liquid platelets or liquid blood cellular products (stored at 22° C.), often producing a local shortage of supplies. Furthermore, current storage practices are conducive to bacterial growth and result in an increased incidence of platelet or blood cell transfusion-associated bacterial sepsis. Other problems associated with platelet transfusion therapy include febrile reactions and HLA (Human Leukocyte Antigen) alloimmunization due to white blood cell (WBC) contamination. Additionally, a risk of viral transmission exists with fresh platelet or blood cell transfusion therapy due to the absence of viral inactivation or removal steps.

The development of a platelet or blood cellular product that provides greater bacterial and viral safety and that has a longer shelf life thus would be advantageous. The ultimate goal is to produce a stabilized blood platelet or blood cellular product that is virally safe, WBC depleted, sterile, stable, and hemostatically effective. A stabilized diafiltered blood product that is storable at room temperature, is lightweight, durable, easy to transport, FDA approved, and has a shelf life of two to five years would be a significant advancement in the management of blood platelet and blood cellular resources. Such a product preferably would be made under Good Manufacturing Practice guidelines using a large-scale method capable of addressing the aforementioned issues and would be gentle enough to prevent extensive activation and aggregation of the platelets.

Lyophilized, or freeze-dried, platelet products are known which are produced using centrifugation methods. See U.S. Pat. No. 5,213,814 to Goodrich, Jr. et al., for example. See also Chao et al., *Infusible platelet membrane microvesicles: a potential transfusion substitute for platelets*, Transfusion 1996, which teaches a method of producing a lyophilized platelet membrane product. Reference also is made to pending U.S. patent applications Ser. No. 891,277, filed May 29, 1992, and Ser. No. 08/424,895, filed Apr. 19, 1995. Centrifugation undesirably causes activation of the platelets, and cannot be scaled up to production levels. Further, the known methods cannot be carried out under sterile conditions, and no viral reduction steps are present in the known methods.

Diafiltration is a known separation process that uses membranes to separate components in a liquid suspension based upon differences in particle size. Depending upon the pore size of the membrane, a component of the liquid suspension can be selectively retained or passed through the membrane. Diafiltration is employed routinely during non-blood cell harvesting applications to separate cells from the acellular medium, but never before has diafiltration been adapted to the production of a blood platelet or blood cellular product.

Accordingly, the need exists for a method to prepare a blood platelet or blood cellular product that does not involve platelet activation, can be scaled up to production levels, and that produces a product that is sterile and virally safe.

SUMMARY OF THE INVENTION

The present invention utilizes diafiltration to overcome the disadvantages of known blood processing techniques.

In accordance with the present invention, diafiltration is utilized to manipulate the liquid medium in which the blood cells are suspended, while preventing extensive activation of those cells. Diafiltration may be used to generate a product that is reduced in undesirable components inherent in plasma, or introduced during the manufacturing process.

The process involves the use of diafiltration either in a single step or in a series of separate or combined processes. The diafiltration of the present invention can be used to remove unwanted plasma proteins from platelets and other blood cells. The process also can be used to add or remove chemical compounds or additives that may, for example, inhibit plasma coagulation or platelet activation, stabilize the platelet, or act as viral inactivation agents in the process. The inventive diafiltration process also can be used to change the medium in which blood cells are suspended, for example, into one that is desirable for long term storage, cryopreservation, or lyophilization. Furthermore, diafiltration can be used as a viral reduction step, producing a separation from the platelets of free viral particles present in plasma from the blood cells.

Specific advantages of the invention relative to blood platelets and blood cells include, but are not limited to, the prevention of extensive activation of platelets, the amenability of the method to large-scale production, the potential to be highly automated, the requirement of minimal space allowances, and the recovery of high yields. The technique can also be operated as a validated closed system, which along with a validated sterilization step incorporated into the procedure, allows a sterile platelet or blood cellular product to be manufactured.

In one particular embodiment, diafiltration, in combination with a method used to stabilize platelets or blood cells by fixation, can be used to generate a sterile, virally-safe product, that is reduced in undesirable components present in plasma, or introduced during the manufacturing procedure.

In one embodiment, a pool of apheresed platelets present in from about 1 liter to about 10 liters of platelet-rich plasma is concentrated to about 1 liter to 2 liters of platelet concentrate. In a first filtration step, this platelet concentrate is diafiltered against multiple exchanges, preferably 8 to 11, of citrated saline buffer to reduce the plasma protein level to below about 0.15 mg/mL, or greater than 99.5% reduction.

The platelets may then be fixed in a 0.01 to 10%, preferably 1–3%, paraformaldehyde solution for a sufficient time, preferably from 5 minutes to 24 hours, and more preferably for about 1 hour at room temperature. The fixation step confers stability to the platelets to withstand freezing, lyophilization, and reconstitution as well as providing a viral and bacterial reduction step.

In a second diafiltration step, the platelets are concentrated and diafiltered against several exchanges, preferably from about 5 to 15 exchanges of a buffer solution, preferably Imidazole Buffered Saline, followed by about 0–6 exchanges against 0.9% NaCl. The approximately 5–21 total exchanges during the second filtration step reduce the formaldehyde level preferably to below 1 ppm. At the end of the second diafiltration step, the platelets are in a saline solution compatible for formulation and lyophilization.

A variety of assays have been developed for the purpose of testing blood platelet and blood cellular products. Such assays can be applied to the diafiltered stabilized blood products of the present invention. These assays include the following:
1) Transmission Electron Microscopy;
2) Platelet Count;
3) Kunicki Score;
4) Platelet Factor 3;
5) Platelet Aggregation;
6) Platelet Agglutination;
7) Hypotonic Shock Response;
8) Thromboxane Generation;
9) Protein Determination;
10) Baumgartner Chamber Annular Perfusion;
11) Scanning Electron Microscopy;
12) Glycoprotein Receptor Sites;
13) Moisture Content;
14) Thromboelastography;
15) Paraformaldehyde Concentration Determination;
16) Rabbit Hemostatic Bleeding Time Model; and
17) Rabbit, Rat and Baboon Circulatory Models; and
18) Flow Cytometric Analyses.

The basic principles and techniques as well as the purpose for each assay have been well defined. Some of these assays are qualitative in nature, while others are quantitative and quite sensitive. Combined, they offer a way of measuring platelet and blood cell structural integrity, shape, response to agonists and hypotonic shock, and adherence to a denuded subendothelial vessel surface. They also provide means of evaluating the integrity of receptor sites and enzyme systems, the degree of activation, and the platelets' ability to participate in the coagulation mechanism and correct a hemostatic dysfunction. These assays are important for guiding the developmental stages of, as well as assessing the overall properties of, the diafiltered stabilized blood product.

These assays demonstrate that the diafiltration process of the present invention produces an overall yield of platelets of from about 50 to about 90%. The platelets produced via this technique show slight, but not extensive activation as evidenced by a Kunicki score of from about 200 to about 260. The fixed platelets have a Ristocetin Agglutination value of from about 30 to about 60%, indicating some loss of function compared to fresh platelets.

Other features and advantages of the present invention will become apparent from the following description of the invention which refers to the accompanying drawings.

DETAILED DESCRIPTION OF THE INVENTION

The present invention is directed to a method of producing a stabilized blood platelet or blood cellular retentate and a plasma protein filtrate by diafiltering whole blood or a blood product against at least one exchange of a buffer and to compositions produced by such method.

The starting materials of the present invention include whole blood and a blood product. Whole blood is used herein to mean blood which contains all its natural constituents and has been deprived of nothing by refining. Whole blood may be collected from any animal source, including, for example, humans, rabbits, rats, baboons, dogs, cats, and other mammals. A blood product starting material is any product derived from whole blood and contains blood plasma. Examples of blood product starting materials suitable for use in the present invention include platelet-rich plasma and platelet concentrate.

Platelet-rich plasma is blood plasma which has present in a certain volume of plasma a greater amount of platelets than would regularly be present in the same volume of a whole blood sample. Platelet-rich plasma is derived from whole blood and is blood plasma which has been refined in order to remove red and white blood cells while retaining platelets. Platelet-rich plasma can be generated by using a variety of techniques known in the art, including, but not limited to, diafiltration, centrifugation, and the use of an apheresis instrument. With typical apheresis machines known in the art, platelets are collected from blood donors. Apheresis machines separate the platelets from the red and white blood cells, resulting in platelet-rich plasma. This platelet-rich plasma is substantially free of red blood cells but may be contaminated with white blood cells.

Platelet concentrate is also a suitable starting material for the present invention. Platelet concentrate is platelet-rich plasma which has been concentrated so that the same amount of platelets which were present in a certain volume of plasma are present in a smaller volume of plasma. For example, a blood sample obtained from a donor by utilizing an apheresis machine would generally yield platelet-rich plasma in an amount ranging from about 250 to about 300 ml. This platelet-rich plasma can then be further concentrated to yield about 50 ml of plasma which would contain therein about the same amount of platelets as were present in the 250–300 ml sample.

The diafiltration of the present invention results in the production of a retentate which comprises a stabilized diafiltered blood product and a plasma protein filtrate. The stabilized blood product retentate is derived from whole blood and includes therein blood platelets, blood cells (such as red cells, white cells, or stem cells), or a mixture of platelets and blood cells. The retentate is substantially free of contaminating plasma proteins. Contaminating plasma proteins are present in the filtrate of the present invention. Examples of plasma proteins removed from the blood platelet retentate and present in the filtrate include albumin, gamma globulins, coagulation factors, complement factors, and protein enzymes and hormones. The retentate of the present invention preferably has a protein level of less than 0.30 mg/ml, more preferably less than about 0.15 mg/ml. The blood product retentate is also substantially free of red blood cells.

The blood product retentate produced by the present invention may optionally contain therein compounds which impart to the retentate certain beneficial attributes, including, for example, viral inactivation, inhibition of platelet activation, and inhibition of blood platelet aggregation. Suitable optional ingredients include anticoagulants, platelet inhibitors, and viral inactivating agents. Anticoagulants suitable for use in the present invention include, for example, EDTA, EGTA, and citrate. Suitable platelet inhibitors include, for example, heparin, antithrombin III, hirudin, prostaglandin, and theophylline. Suitable viral inactivating agents include, for example, paraformaldehyde, glutaraldehyde, solvent detergent, psoralen, B-propiolactone, and phthalocyanine dyes.

The present blood product retentate may be suspended in a variety of media, including those which are desirable for long-term storage, cryopreservation, or lyophilization. Suitable embodiments of such media include, for example, albumin, disaccharides, monosaccharides, trehalose, and antifreeze proteins.

The blood product retentate of the present invention is stabilized, such that it is able to be stored at room temperature, is durable, and has a shelf life longer than five days.

In the present invention, the blood product starting material is diafiltered against at least one exchange of a buffer. A diafiltration exchange of blood or blood product means that the cellular components of the blood or blood product (including blood cells and platelets) remain on one side of a separation membrane, while the non-cellular components are washed through the membrane under prescribed conditions of flow rate, pressure, membrane pore size, and buffer composition and volume. In embodiments utilizing multiple exchanges, the blood or blood product starting material is preferably diafiltered against from about 5 to about 15 exchanges of buffer, more preferably from about 8 to about 12 exchanges, and more preferably against 10 exchanges.

The buffers suitable for use in the diafiltration exchanges include buffers known in the art for use in diafiltration. Preferred buffers include those in the phosphate, citrate, and imidazole families. More preferably, suitable buffers include saline and citrated saline. The buffers may be categorized as either processing buffers (those used during diafiltration steps) or fixation buffers (those used during fixation steps). The processing buffers are preferably selected from saline buffers. The fixation buffers preferably are selected from phosphate buffers, ACD buffer, imidazole buffers, formaldehyde, paraformaldehyde, and glutaraldehyde buffers, or buffers containing solvent detergents, psoralens, B-propiolactone, or phthalocyanine dyes.

The volume of buffer used varies with the volume of the blood or blood product starting material to be diafiltered according to the present invention. Preferably, the volume of buffer used ranges from about one to about 100 liters. The concentration of the buffers used can range from about 1 mM to about 1.0 M, preferably from about 5 mM to about 300 mM.

The buffers may contain optional ingredients, including, for example, a platelet inhibitor or an anticoagulant or salts such as NaCl to maintain physiological osmolarity. A platelet inhibitor is a compound which prevents activation of platelets. Suitable platelet inhibitors include, for example, heparin, antithrombin III, hirudin, prostaglandin, and theophylline. Anticoagulants suitable for use in the present invention are broad chelating agents, and are preferably selected from the group including EDTA, EGTA, and citrate.

Various types of membranes are suitable for use with this invention. Preferred membranes are made of vinyl, nylon, or hollow fiber construction with pore size ranging from about 0.1 micron to about 1.0 micron.

The diafiltration of the present invention can be performed with either single or multiple diafiltration steps. The process may also optionally include a fixation step. The fixation step confers stability to the platelets to withstand freezing, lyophilization and reconstitution. The fixation step also functions as a viral and bacterial reduction step. The fixation step is generally performed after at least one diafiltration step. In the fixation step, a fixing solution is added to the platelet-containing portion of the previous diafiltration. Suitable fixing solutions include formaldehyde, paraformaldehyde, glutaraldehyde, and isopropanol, more preferably formaldehyde and paraformaldehyde.

One embodiment of the present invention for preparing a diafiltered stabilized blood product using diafiltration technology will be described with reference to FIGS. 1 through 4. The inventive method includes up to three steps, illustrated in the flow chart of FIG. 1 as follows: a prefixation diafiltration step ("DF1"); a fixation step; and a post-fixation diafiltration step ("DF2").

Figure 1:
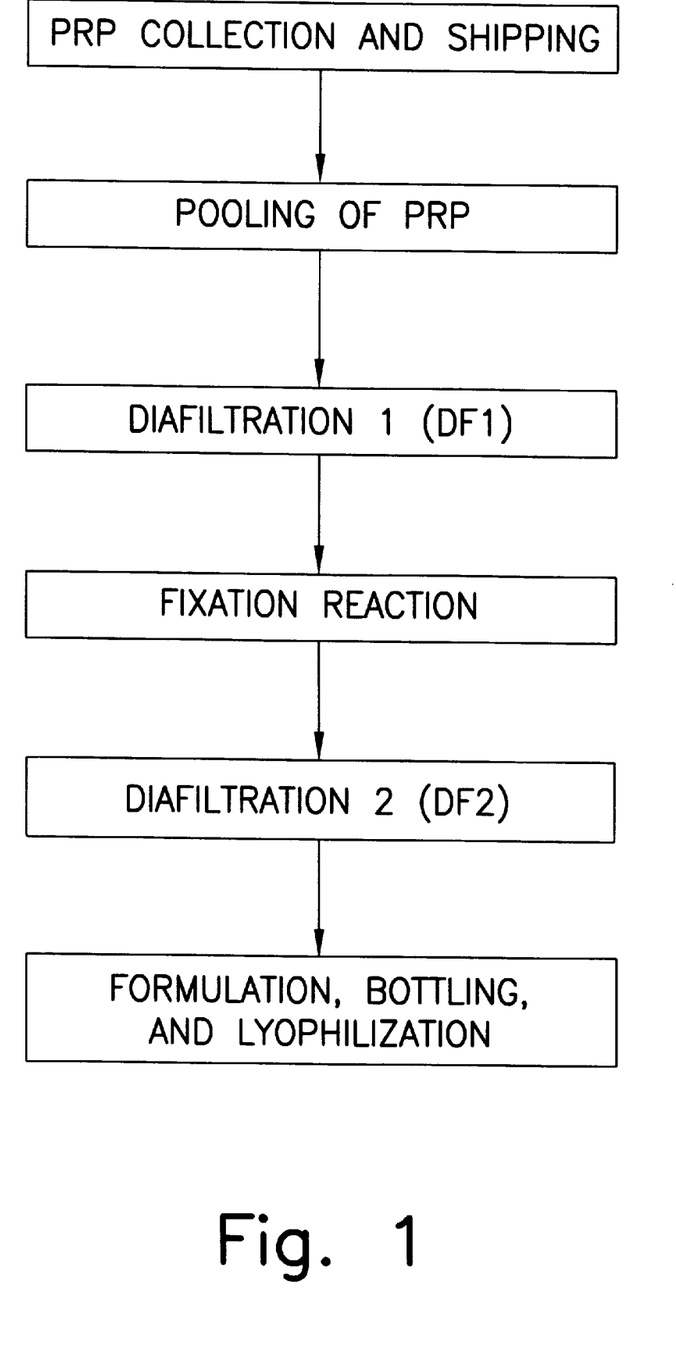
FIG. 1 is a generalized overview diagram of a platelet processing procedure according to the present invention.

In the DF1 step, a pool of apheresed platelets in platelet-rich plasma ($3 \times 10^{12}$ platelets in 3 liters) is concentrated to 1–2 liters and then diafiltered against 8–11 exchanges of citrated saline buffer to reduce the plasma protein level to below 0.15 mg/mL. This step by itself can be used to prepare a plasma-free platelet product when the proper stabilizers are subsequently added.

In the fixation step, the platelets are fixed in a 0.1 to 2% paraformaldehyde solution for up to 1 hour at room temperature. The fixation step confers stability to the platelets to withstand freezing, lyophilization, and reconstitution as well as providing a viral and bacterial reduction step.

In the DF2 step, the platelets are concentrated and diafiltered against 8–11 exchanges of Imidazole Buffered Saline, followed by 3 exchanges against saline. The 11–14 total exchanges during the DF2 step reduce the formaldehyde level to below 1 ppm. At the end of the DF2 step the platelets are in a saline solution compatible for formulation (5% Human Serum Albumin in 0.9% NaCl) and lyophilization.

As shown below in Table 1, the diafiltration of the present invention produces an overall yield of platelets between 61–71%. The platelets produced via this technique show slight, but not extensive activation as evidenced by a Kunicki score ranging between 216 and 260. The fixed platelets have a Ristocetin Agglutination value of 37–41%, indicating some loss of function compared to fresh platelets. The ranges of the DF1 yield, DF2 yield, Overall yield, and Ristocetin Agglutination on three identically processed lots were small (73–81%, 84–92%, 61–71%, and 37–41% respectively) demonstrating a high degree of reproducibility associated with this technique.

As set forth below, thrombocytopenic rabbits are used to test the hemostatic effectiveness of the diafiltered blood products produced according to the present invention.

The in vivo functionality of a diafiltered platelet product produced by the present invention was demonstrated in a Thrombocytopenic Rabbit Ear Bleeding Model. As shown in Table 2, ethyl-palmitate treated thrombocytopenic rabbits infused with $5 \times 10^{10}$ of three identically produced lots of lyophilized platelets all showed marked corrections of bleeding times from >2700 seconds (untreated) down to an average of 413 to 534 seconds one hour after infusion, and 540 to 620 seconds four hours after infusion.

Pilot Scale Procedure

A method of diafiltering platelets according to one embodiment of the present invention is described below for pilot scale manufacturing of lyophilized paraformaldehyde-fixed platelet preparations. This procedure is based upon a laboratory bench scale protocol and employs diafiltration technology using microfiltration membranes.

Processing Buffers and Solutions:

Processing buffers used during the diafiltration procedure of the present invention were prepared using pyrogen-free water for injection. The buffers were sterile filtered into clean vessels through a 0.22 µm membrane to remove particulates and endotoxins that may have been present. The buffers utilized were as follows:

Citrated Saline Buffer (CS)—5.4 mM $Na_3$ Citrate, 146 mM NaCl, pH adjusted to 6.5 at 25° C. with HCl.

Imidazole Buffered Saline (IBS)—84 mM Imidazole, 146 mM NaCl, pH adjusted to 6.8 at 25° C. with HCl.

Saline—146 mM NaCl.

Fixation Buffers and Solutions:

Fixation buffers required for the intermediary fixation step between the first (DF1) and second (DF2) diafiltration steps were as follows:

Phosphate Buffer—270 mM $NaH_2PO_4$, pH adjusted to 6.5 at 25° C.

ACD Buffer—170 mM $Na_3$Citrate $2H_2O$, 129 mM Citric Acid Monohydrate, 222 mM Dextrose, pH adjusted to 4.5 at 25° C.

8% Paraformaldehyde Buffered Solution (PFA)—Paraformaldehyde (2.67 M) was suspended in WFI water and was dissolved by adjusting the pH to 11 through the periodic addition of 50% NaOH, until the solution was clear. After the paraformaldehyde was dissolved thoroughly, $NaH_2PO_4$ (270 mM) was added and the pH was adjusted to 7.2 at 25° C. with HCl. The solution was brought to volume with water for injection.

Paraformaldehyde Fixation Solution (PFS)—One part ACD Buffer was mixed with 9 parts 5% PFA Buffer and 10 parts Phosphate Buffer. The pH was adjusted to 6.8 at 25° C. with concentrated HCl and/or NaOH. The solution was sterile filtered through a 0.22 µm membrane.

Overview of Method

The manufacturing procedure can be divided into three steps: 1) Diafiltration 1 (DF1); 2) Paraformaldehyde Fixation; and 3) Diafiltration 2 (DF2) (FIG. 1). In the first step (DF1) fresh or stored platelets, or other blood cells are pooled and diafiltered to remove plasma proteins. The technique used during DF1 must be gentle enough to prevent the activation and aggregation of the platelets. The Paraformaldehyde Fixation step stabilizes the platelets to withstand freezing, lyophilization and subsequent reconstitution. Furthermore, the Paraformaldehyde Fixation step can also provide a viral and bacterial reduction. The objective of the Diafiltration 2 step is twofold: 1) to remove the paraformaldehyde to undetectable levels; and 2) to suspend the platelets into a formulation buffer for subsequent lyophilization. The procedure for each step is described in further detail below.

Diafiltration System

Figure 2:
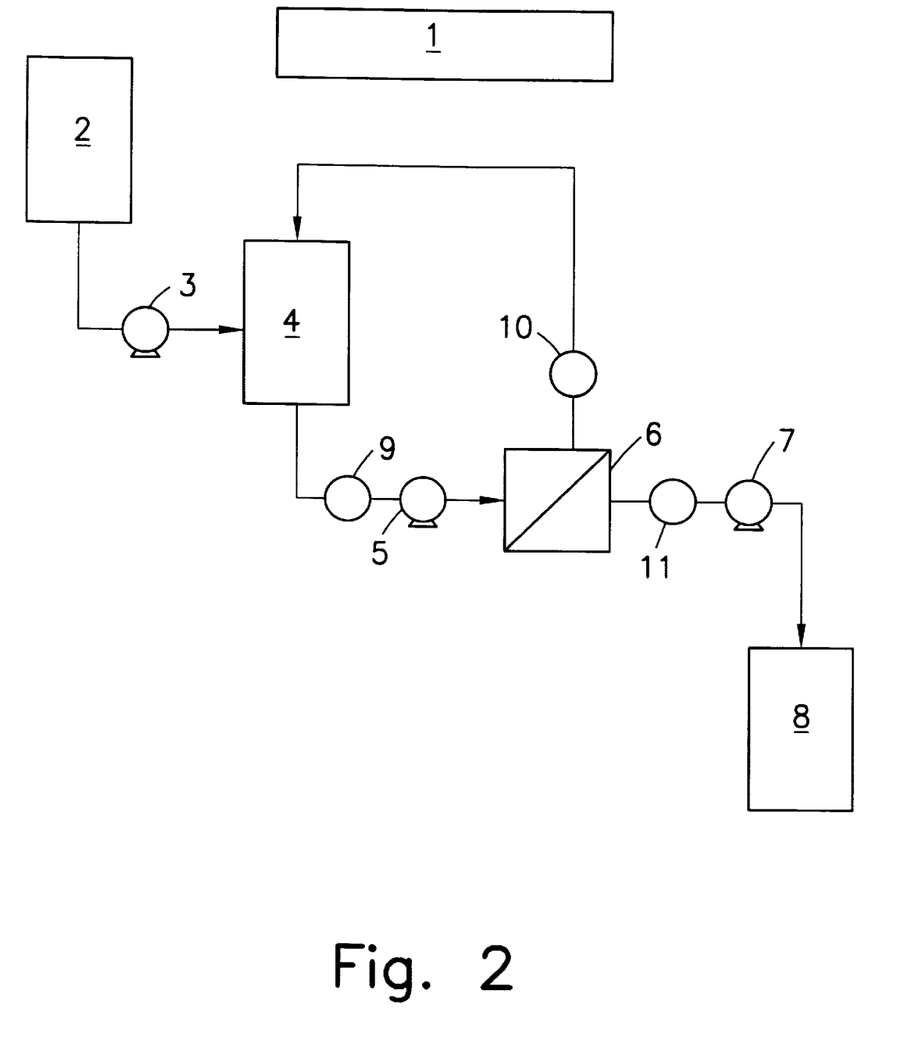
FIG. 2 is a block flow diagram of a three-pump diafiltration system according to the present invention.

One embodiment of the diafiltration procedure of the present invention can be carried out using the processing system illustrated in FIG. 2. The system was composed of: a control unit 1; a buffer tank 2; a buffer pump 3; a processing tank 4; a feed pump 5; a filter holder 6; a permeate pump or a control valve 7; a waste container 8; feed, permeate, and retentate pressure gauges 9, 10, 11; feed, permeate, and retentate valves (not shown); and a heat exchanger (not shown). The control unit consisted of controls for regulating the feed and permeate pump speeds and digital readouts for monitoring the pressure, temperature, and flow rate.

Integrity Test of Membranes

Prior to DF1 or DF2, a single microfiltration membrane (4 ft$^2$) was mounted into the filter holder 6. The membrane was wetted with WFI water (10 L/min, Retentate pressure=2–3 psi, 10 min) and a water permeability test and air diffusion integrity test were performed as described by the manufacturer. The system was rinsed (10 L/min, $P_{ret}$=2–3 psi, 5 min) with either 2 L of CS Buffer (DF1) or 2 L of Saline (DF2) and drained.

Collection of PRP

In an embodiment of the present invention, platelet-rich plasma can be used as a starting material. In one particular embodiment, Platelet-rich Plasma (PRP) was collected as single donor units in ACD using either a Haemonetics or COBE apheresis instrument. The platelets were tested for a variety of infectious agents, and if negative, were released. The single donor units of PRP (400 mL; $1.2 \times 10^6$ platelets/µL) were shipped overnight in specially designed insulated boxes that allowed for adequate gas exchange to the platelets, while maintaining the temperature at 20–25° C. Upon arrival, the platelets were pooled, mixed, and counted. The platelet pool was assayed for Hypotonic Shock Response; Arachidonic acid, Collagen, a dual agonist (ADP and Arachidonic acid) aggregation response; and Ristocetin agglutination.

DF1

One objective of DF1 is to use diafiltration to wash out plasma proteins from a solution of blood platelets, blood cells, or a mixture of platelets and blood cells, while minimizing the activation and aggregation of the blood platelets or blood cells. A suitable embodiment of the diafiltration procedure is outlined in FIG. 2.

In an embodiment of the invention, the PRP pool ($3 \times 10^{12}$ platelets, ≈2–3 L) was poured into the processing tank 4. The retentate valve was opened completely, and the feed pump started 5 (2 L/channel/min; i.e., for a 4 ft$^2$ membrane with 5 channels, 10 L/min). The permeate pump 7 was adjusted to achieve the desired flux rate (10–90 L/m$^2$/h;). The permeate flow was diverted to a waste container 8 and the platelets were concentrated to a volume of approximately 2 L. The platelets were then diafiltered at a constant volume (2 L against CS Buffer for 8 exchanges (16 L)) using a flux rate of 10–95L/m$^2$/h. A constant volume was maintained by regulating the input of CS Buffer into the processing tank 4 via the buffer pump 3. After approximately 8 exchanges had been completed, the buffer pump 3 was stopped, and the platelets were concentrated to the maximal allowable level (0.8–1.0 L), at which point the feed and retentate pumps were stopped. The platelets were emptied through a low-point drain valve into a tank for the fixation reaction. The system was rinsed twice by recirculating CS Buffer (10 L/min), with the permeate valve closed and the permeate pump in the off position. The two rinse volumes were added to the platelets, and the volume was adjusted to 4 L with CS Buffer for the fixation reaction.

Paraformaldehyde Fixation Reaction

In this embodiment of the invention, the platelets from DF1 (4 L; 4–8×10⁵ platelets/μL) were placed into a stainless steel vessel, and 4 L of Paraformaldehyde Fixation Solution were added and thoroughly mixed. The platelet concentration during fixation was approximately 300,000/μL. The vessel was covered and allowed to react at room temperature (22–26° C.) for 60 minutes with no further agitation.

DF2

The 8 L of platelet suspension from the fixation reaction was placed into the processing reservoir. The retentate valve was opened completely and the feed pump was started (2 L/channel/min; i.e., 10 L/min for a 4 ft² membrane). The permeate pump was adjusted to achieve the desired flow rate of 10–95 L/m²/h. The permeate flow was diverted to a waste receptacle, and the platelets were concentrated to a volume of approximately 2 L. The platelets were then diafiltered at a constant volume (2 L) against IBS for 11 exchanges (22 L) and then against Saline for a further 3 exchanges (6 L). A constant volume was maintained by regulating the input of IBS or Saline into the processing tank via the buffer pump. After the 14 total exchanges were completed, the buffer pump was stopped, and the platelets were concentrated to the maximal allowable level (≈1 L), at which point the feed and retentate pumps were stopped. The platelets were emptied through a low-point-drain valve into a tank for final formulation. Two additional rinses of the system were done with saline to determine the maximal attainable recovery of platelets.

Formulation and Lyophilization

Human serum albumin (Albuminar-25, Centeon) was added to bring the final platelet suspension to 5% HSA in 0.9% NaCl (pH 6.8±0.2) at a final platelet concentration of 500,000–3,000,000 plts/μL. The platelets were lyophilized and stored at –20° C. or –70° C. until further use.

Protein Removal Assay

The level of protein remaining within the retentate fluid during DF1 was monitored by an absorbance assay at 280 nm. Samples (2 mL) were withdrawn at desired intervals from the processing reservoir. The samples were centrifuged (16,000 RPM, 10 min) in 1.5 mL Eppendorf tubes in an Eppendorf 5415C microcentrifuge. The supernatant was removed, taking care not to disturb the platelet pellet, and transferred to a clean tube. The $A_{280}$ value was determined in a Beckman DU 640 Spectrophotometer using Citrated Saline Buffer as a blank. The protein content was estimated using an extinction coefficient of 1.0 cm²/mg.

Formaldehyde Assay

The level of formaldehyde remaining in the retentate fluid during DF2 was monitored using a calorimetric formaldehyde assay. Aliquots (3 mL) were removed from the processing reservoir at desired intervals and were immediately centrifuged (16,000 RPM, 8 min) in 1.5 mL Eppendorf tubes in an Eppendorf 5415C Microcentrifuge. The supernatant was removed, taking care not to disturb the platelet pellet, and transferred to a clean 15 mL plastic centrifuge tube, capped, and frozen at –20° C. until assayed.

Rabbit Ear Bleeding Time Experiments

The hemostatic effectiveness of lyophilized platelets was determined from ear bleeding time experiments conducted in thrombocytopenic rabbits. For these experiments, 5×10¹⁰ lyophilized platelets were injected into each thrombocytopenic rabbit and the correction in the bleeding time was determined, in duplicate, at one and four hours post-infusion. Three identically processed lots were tested, and a total of 8 rabbits were infused per lot. The ear bleeding time of normal rabbits is approximately 250 seconds, while the ear bleeding time of thrombocytopenic rabbits is greater than 2700 seconds. The platelets tested were prepared using the diafiltration method described above, except that Saline was substituted for Imidazole Buffered Saline throughout the DF2 procedure.

Cleaning of Membranes

Membranes were designated for DF1 or DF2 usage only. A single membrane may be used for more than one production lot. The membranes were cleaned after each use and were tested for their water permeability and air integrity priorities prior to reuse. The membranes were cleaned in place with a bleach solution (4 L, 600 ppm hypochlorite, 50° C.) as suggested by the manufacturer. Using the bleach solution, the membranes were rinsed twice (10 L/min, $P_{perm}$=3.0 psi, 2–5 min) followed by an extended wash cycle (10 L/min, $P_{perm}$=3.0 psi, 30 min).

RESULTS

Protein Removal During DF1

Figure 3:
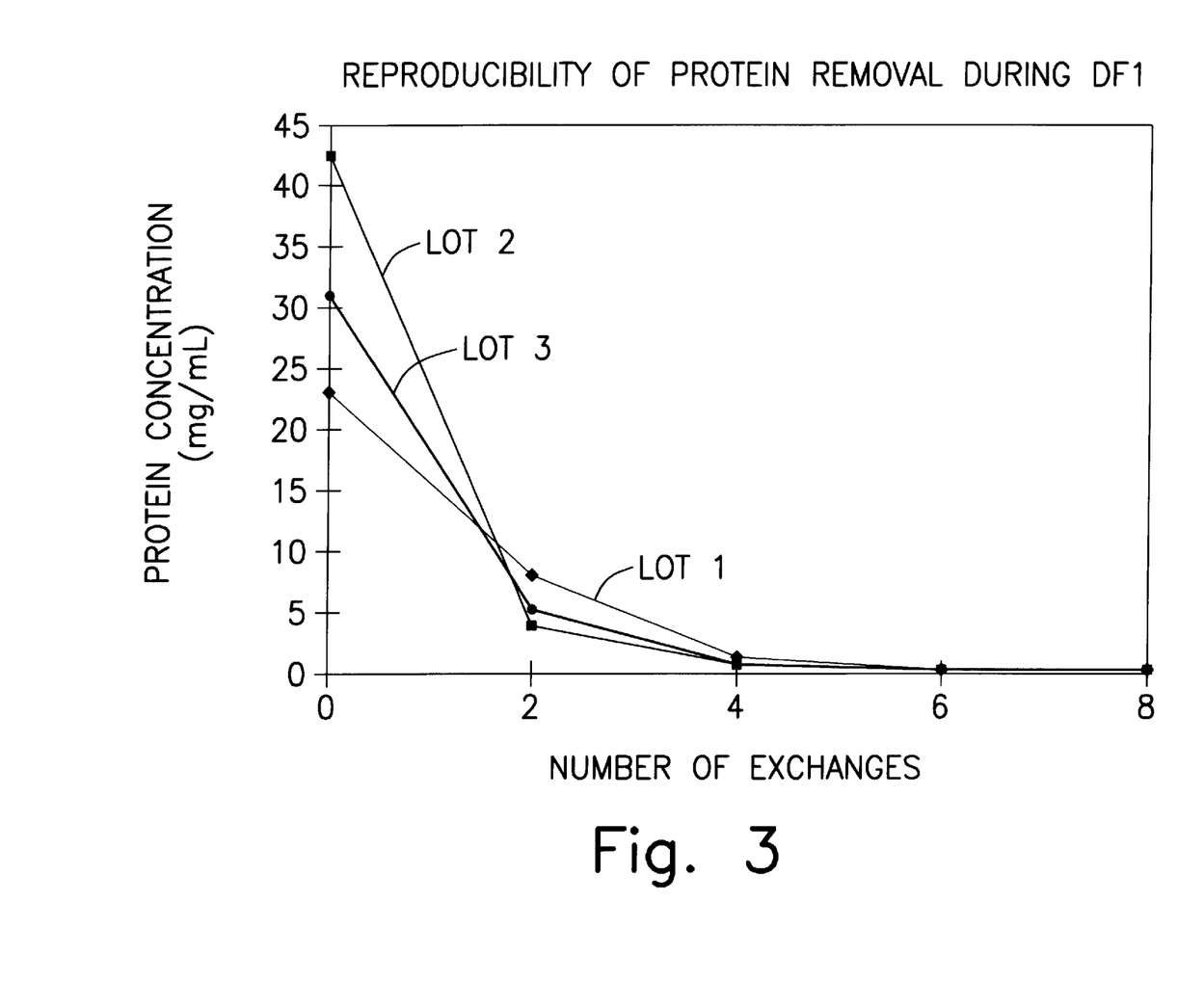
FIG. 3 is a graph showing protein removal during a first diafiltration step according to the present invention.

The removal of plasma proteins from the blood product during DF1 is shown in FIG. 3. The lots shown were run under identical typical processing conditions (45 L/m₂/h, 2 L/min/channel; 0.22 μ 4 ft² PVDF Durapore membrane). At the end of 8 buffer exchanges, greater than 99.5% of the plasma protein was removed, such that the protein level was below 0.15 mg/mL, as shown in Table 1.

TABLE 1

RESIDUAL PROTEIN LEVELS AFTER DIAFILTRATION 1

| LOT NO. | PROTEIN CONCENTRATION (mg/mL) |
|---|---|
| 1 | 0.11 |
| 2 | 0.11 |
| 3 | 0.11 |

Formaldehyde Removal During DF2

Figure 4:
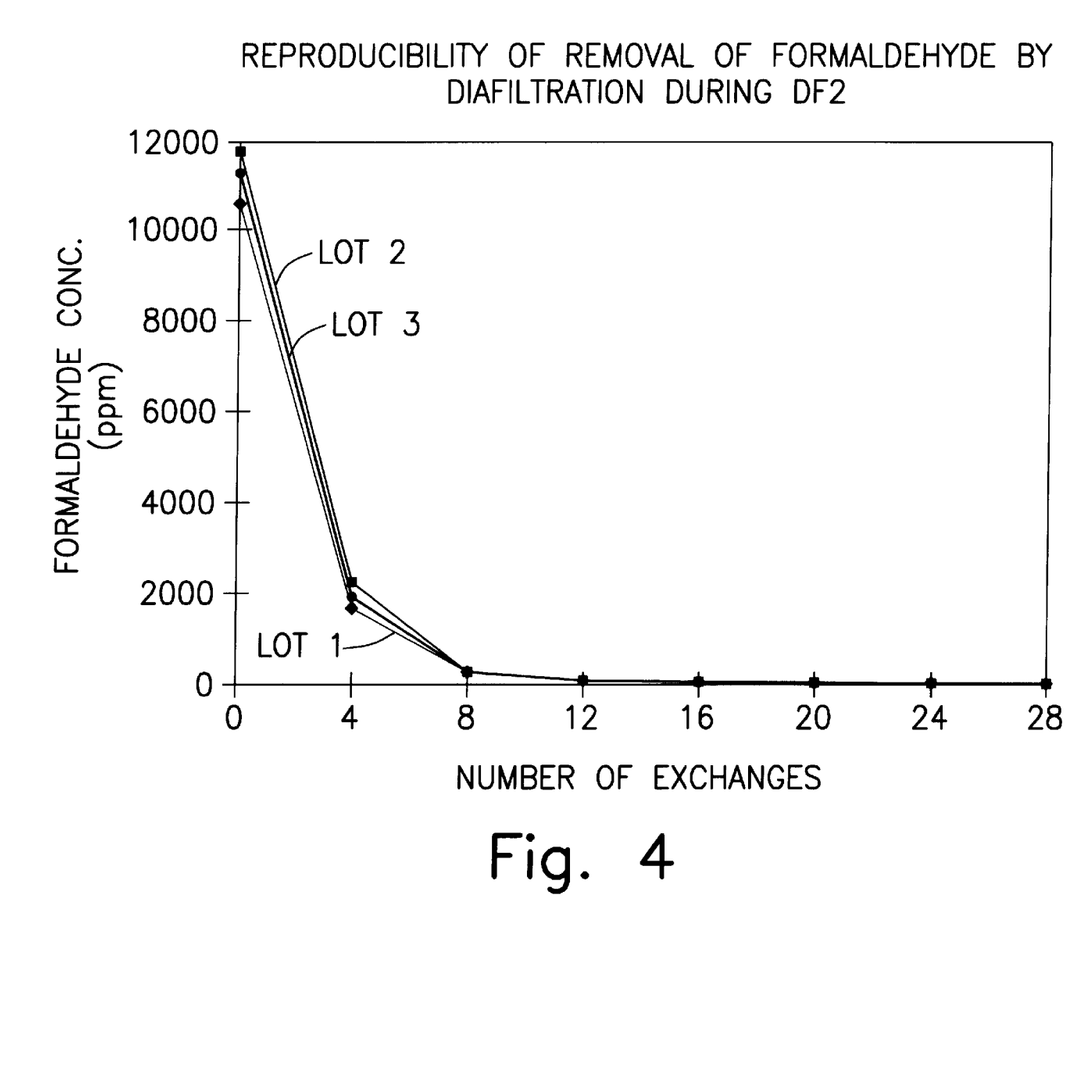
FIG. 4 is a graph showing formaldehyde removal during a second diafiltration step according to the present invention.

The removal of formaldehyde from the blood product during DF2 is shown in FIG. 4. In order to determine the ability of the diafiltration technique to effectively remove paraformaldehyde from the blood product suspension, the platelets generated by an embodiment of the invention were diafiltered against 12 exchanges of saline rather than the normal IBS buffer. The 3 lots shown were run under identical processing conditions (45 L/m²/h, 2 L/min/channel; 0.22 μ ft²). The results showed that formaldehyde was removed effectively and reproducibly between the three runs. At the end of 12 buffer exchanges the free formaldehyde level had been reduced to below 1 ppm, as shown in Table 2.

TABLE 2

RESIDUAL FORMALDEHYDE LEVELS AFTER DIAFILTRATION 2

| LOT NO. | FORMALDEHYDE CONCENTRATION (ppm) |
|---|---|
| 1 | <1 |
| 2 | <1 |
| 3 | <1 |

Recoveries and In Vitro Assay Characteristics of Platelets and Blood Cellular Products Processed By Diafiltration The diafiltration process may be controlled by adjusting the flow rates and permeate flux rates to desired levels. In one embodiment the entire process is run using pre-set flow and flux rates that are not adjusted during the process in response to changes in retentate, permeate or transmembrane pressures.

Three lots of platelets (Table 3) were processed under identical conditions using the processing protocol described herein. The processing recoveries, Kunicki Scores, and Ristocetin Agglutination Values of each lot were within narrow ranges indicating good reproducibility of the method. The bleeding time corrections (Table 4) also showed good reproducibility at both one hour and four hours post-infusion.

TABLE 3

RECOVERIES, KUNICKI SCORE, AND RISTOCETIN AGGLUTINATION VALUES ON LYOPHILIZED PLATELETS PREPARED BY DIAFILTRATION

| LOT NO. | | RECOVERY (%) | | | KUNICKI SCORE | RISTOCETIN AGGLUTIN-ATION (%) |
| --- | --- | --- | --- | --- | --- | --- |
| | | DF1 | DF2 | OVERALL | | |
| 1 | | 73.1 | 83.6 | 61.2 | 216 | 38.0 |
| 2 | | 77.2 | 92.4 | 71.3 | 223 | 37.0 |
| 3 | | 80.5 | 83.6 | 67.3 | 260 | 41.0 |
| THREE OPTIMIZED DF LOTS | RANGE | 73–81 | 84–92 | 61–71 | 216–260 | 37–41 |

TABLE 4

CORRECTION OF BLEEDING TIMES OF THROMBOCYTOPENIC RABBITS BY DIAFILTERED PLATELETS AT 1 AND 4 HOURS POST-INFUSION

| | One Hour Post-Infusion | | Four Hours Post-Infusion | |
| --- | --- | --- | --- | --- |
| LOT NO. | Platelet Count (plts/μL × $10^3$) | Bleeding Time (sec.) | Platelet Count (plts/μL × $10^3$) | Bleeding Time (sec.) |
| 1 | 125.5 | 413 | 46.8 | 540 |
| 2 | 113.6 | 481 | 42.3 | 617 |
| 3 | 145.3 | 534 | 57.4 | 562 |
| RANGE | 113.6–145.3 | 413–534 | 42.2–57.4 | 540–617 |

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A method of preparing a stabilized cellular blood product by diafiltering a starting material to produce a cellular retentate and a filtrate, the method comprising diafiltering the starting material against at least one exchange of a buffer, wherein the starting material comprises whole blood or a blood product, the cellular retentate comprises a diafiltered stabilized cellular blood product, and the filtrate comprises contaminating plasma proteins.

2. The method of claim 1 wherein the whole blood is collected from a mammalian source.

3. The method of claim 2 wherein the whole blood is collected from a human source.

4. A method of preparing a stabilized blood product by diafiltering a starting material to produce a retentate and a filtrate, the method comprising diafiltering the starting material against at least one exchange of a buffer, wherein the starting material comprises platelet-rich plasma or platelet concentrate, the retentate comprises a diafiltered stabilized blood product, and the filtrate comprises contaminating plasma proteins.

5. The method of claim 4 wherein the buffer contains a platelet inhibitor or an anticoagulant.

6. The method of claim 5 wherein the platelet inhibitor is selected from the group consisting of heparin, antithrombin, hirudin, prostaglandin, and theophylline.

7. The method of claim 5 wherein the anticoagulant is selected from the group consisting of EDTA, EGTA, and citrate.

8. The method of claim 4 wherein the diafiltered stabilized blood product comprises blood platelets, blood cells, or a mixture of blood platelets and blood cells.

9. A method of preparing a stabilized blood product by diafiltering a starting material to produce a cellular retentate and a filtrate, the method comprising:

diafiltering the starting material against at least one exchange of a buffer, wherein the starting material comprises whole blood or a blood product, the cellular retentate comprises a diafiltered blood product, and the filtrate comprises contaminating plasma proteins; and stabilizing the cellular retentate.

10. The method of claim 9, wherein the step of stabilizing comprises adding to the retentate amino acids, albumin, trehalose, antifreeze proteins, monosaccharides, disaccharides, or inhibitors.

11. The method of claim 9, wherein the step of stabilizing comprises fixation of the cellular retentate.

12. The method of claim 1, further comprising the step of reducing viral and bacterial activities of the retentate.

13. The method of claim 12, wherein the retentate comprises platelets, and the step of reducing viral and bacterial activities comprises fixing the platelets to produced fixed platelets.

14. The method of claim 13, wherein the fixed platelets are diafiltered against saline.

15. The method of claim 13, further comprising the step of adding a buffered saline solution to the fixed platelets.

16. The method of claim 15, wherein the buffered saline solution is imidazole buffered saline.

17. The method of claim 1, wherein the buffer is citrated saline.

18. The method of claim 17, wherein the starting material is diafiltered against between about 8 to about 11 exchanges of citrated saline.

19. The method of claim 18, wherein the retentate contains plasma proteins at a level of less than about 0.15 mg/mL.

20. The method of claim 1, further comprising the step of concentrating the cellular retentate.

* * * * *